(12) United States Patent  
Bagwell

(10) Patent No.: US 10,104,885 B2
(45) Date of Patent: Oct. 23, 2018

(54) PEST CONTROL FILMS AND METHODS FOR MAKING SAME

(71) Applicant: ProvisionGard Holdings, LLC, Greensboro, NC (US)

(72) Inventor: James Bagwell, Greensboro, NC (US)

(73) Assignee: PROVISIONGARD HOLDINGS, LLC, Greensboro, NC (US)

( * ) Notice: Subject to any disclaimer, the term of this patent is extended or adjusted under 35 U.S.C. 154(b) by 300 days.

(21) Appl. No.: 13/955,417

(22) Filed: Jul. 31, 2013

(65) Prior Publication Data

US 2014/0037706 A1 Feb. 6, 2014

Related U.S. Application Data

(60) Provisional application No. 61/677,611, filed on Jul. 31, 2012.

(51) Int. Cl.
*A01N 25/10* (2006.01)
*B29D 7/01* (2006.01)
*A01N 25/34* (2006.01)

(52) U.S. Cl.
CPC .............. *A01N 25/10* (2013.01); *A01N 25/34* (2013.01); *B29D 7/01* (2013.01)

(58) Field of Classification Search
CPC ........... A01N 49/00; A01N 25/34; B29D 7/01
See application file for complete search history.

(56) References Cited

U.S. PATENT DOCUMENTS

| 5,688,509 A | 11/1997 | Radwan et al. |
|---|---|---|
| 5,843,215 A | 12/1998 | Whalon et al. |
| 7,204,994 B2 | 4/2007 | Leeper et al. |
| 7,250,396 B2 | 7/2007 | Leeper et al. |
| 7,977,305 B2 | 7/2011 | Leeper et al. |
| 2003/0203229 A1 | 10/2003 | Aral et al. |
| 2004/0034149 A1* | 2/2004 | Garcia .................. A01N 65/00 524/474 |
| 2004/0151748 A1 | 8/2004 | Leeper et al. |
| 2005/0158537 A1 | 7/2005 | Aral et al. |
| 2005/0158569 A1 | 7/2005 | Aral et al. |
| 2005/0208157 A1* | 9/2005 | Navarro ................. A01N 31/02 424/756 |
| 2011/0256195 A1* | 10/2011 | Heinemann ........... A01N 53/00 424/403 |

FOREIGN PATENT DOCUMENTS

| FR | 2938277 | 5/2010 |
|---|---|---|
| JP | 2002-036466 | 2/2002 |

OTHER PUBLICATIONS

International Search Report and Written Opinion for PCT/US2013/052921 dated Feb. 17, 2014.

* cited by examiner

*Primary Examiner* — Michael B. Pallay
(74) *Attorney, Agent, or Firm* — Kilpatrick Townsend & Stockton LLP

(57) ABSTRACT

Pest control compositions and methods for forming a pest control composition, comprising the steps of providing a lower polymer weave; providing an upper polymer film; and mixing a pest control agent with a polymer and extruding the resulting mixture between the lower polymer weave and the upper polymer film are discussed. In addition, methods of forming a pest control composition comprising providing a lower polymer weave layer and mixing a pest control agent with a polymer and extruding the resulting mixture on the lower polymer weave layer and pest control compositions formed by such processes are discussed. Also described are pellets and monolayer films of pest control agent and polymer.

16 Claims, No Drawings

PEST CONTROL FILMS AND METHODS FOR MAKING SAME

PRIORITY CLAIM

The present application claims priority to U.S. Provisional Application No. 61/677,611, filed Jul. 31, 2012, the entire contents and disclosure of which is hereby incorporated by reference.

FIELD OF THE INVENTION

This invention relates to preventing pest infestation in packaging structures. More particularly, the invention relates to pest control compositions and specifically to hormone-containing and pesticide-containing polymer compositions for use in food packaging.

BACKGROUND OF THE INVENTION

The infestation of food products by insects and insect larvae is well-documented. One particularly destructive pest is the Indian Meal Moth, *Plodia Interpunctella*, which is known to infest stored commodities, processed foods packaged for human consumption, and products produced for the pet food and birdseed markets. Infestations often remain hidden until the final larval stage, called the wandering phase, begins in which the larvae begin to search for a pupation site. Most Lepidopteran larvae become more tolerant of insecticides as they age. As a result, wandering-phase Indian Meal Moth larvae can be difficult to control.

Conventionally, coatings which repel insects, discourage feedance and deter oviposition have been implemented on food product packaging materials. For example, U.S. Pat. No. 5,843,215 to Whalon et al. is directed to coatings which comprise a water-based or water soluble resin and plant secondary compounds. The plant secondary compounds consist of those compounds which have insecticidal characteristics, such as insect repellence, antifeedance and oviposition deterrence.

U.S. Pat. No. 5,688,509 to Radwan et al. is directed to a controlled-release insect repellant device and a method for repelling insects from food, tobacco, or other consumable items. The device comprises an insect repellent composition contacting a substrate. The device is prepared by a method comprising applying the insect repellent composition to the substrate wherein the repellent compound used is present in the controlled-release insect repellent device in an amount such that when it is released it is non-toxic to humans and animals. The method for repelling insects comprises placing the controlled-release insect repellent device in an area where insects may be present. The insect repellent composition comprises a repellent compound and a controlled-release agent which comprises a compound which may be synthetic and/or natural, and, optionally, a solvent. The repellent compound may be chosen from the group consisting of essential oils and active ingredients of essential oils.

Although pesticidal compounds have been used with some success on food packaging materials, the toxicity of these compounds sometimes renders them unsuitable for use on food packaging materials. Some insect juvenile hormones, their analogues and their derivative compounds, present less toxicity than conventional pesticidal compounds. Juvenile hormones are insect growth regulators, which interfere with the developmental process of immature insects, but do not necessarily kill adult insects. In February 2002, the insect growth regulator methoprene was relabeled for stored commodities at application rates of 1, 2.5 and 5.0 wppm.

Methoprene and many other hormones are relatively volatile. As a result, conventional means for delivering pesticidal compounds may be undesirable for delivering hormones because the hormone may volatize at an undesirably fast rate thereby providing an unsatisfactory product lifetime. U.S. Pat. No. 7,250,396, the entirety of which is incorporated herein by reference, describes a hormone composition including a substrate having an external surface, and a coating layer including a polymer web, a UV protectant material, and from about 1 wppm to about 100,000 wppm of a hormone dispersed throughout the polymer web disposed on the external surface. A problem with many hormone containing coatings is that the hormone may be exposed to ambient conditions, which limits the effective active lifetime of the hormone.

Accordingly, the need exists for new packaging structures having desirable pest control delivery characteristics and product lifetime.

SUMMARY OF THE INVENTION

The present invention provides pest control film compositions having desirable pest control agent delivery characteristics and product lifetime. The film compositions of the present invention preferably are implemented in human and animal food packaging materials in order to safely and efficiently protect the foodstuffs contained therein from insect infestation. In one embodiment, the invention is directed to a method for forming a pest control composition comprising the steps of: providing a lower polymer weave; providing an upper polymer film; mixing a pest control agent with a polymer and extruding the resulting mixture between the lower polymer weave and the upper polymer film. The polymers of the various layers may comprise, for example, polyethylene or propylene or blends thereof. The pest control agent optionally is added at a concentration from 0.01 wt. % to 5 wt. %, based on the total weight of the extruded material. Optionally, the pest control agent can be a pesticide or a hormone, such as a juvenile hormone, which may be selected from, for example, one or more of hydroprene, methoprene, kinoprene and/or triprene.

Another aspect of the invention is a method for forming a pest control composition comprising the steps of: providing a lower polymer weave; mixing a pest control material with a polymer and extruding the resulting mixture with the lower polymer weave.

Another aspect of the invention is a method for forming a pest control composition comprising the steps of mixing a pest control agent with a first polymer composition and extruding the mixture, cooling the extruded mixture, and pelletizing the cooled, extruded mixture into pellets containing the pest control agent. The pellets containing the pest control agent can be combined with a second polymer composition and extruded as a monolayer or multilayer film. The films might even later be combined with other films using laminating adhesives.

DETAILED DESCRIPTION OF THE INVENTION

The present invention relates to pest control material-containing film and laminate compositions having desirable pest control delivery characteristics and product lifetime. The pest control material-containing film can be prepared from at least one pest control material and at least one polymer, which can be mixed and extruded into a film. The resulting pest control material-containing film can be utilized in a variety of laminates, for example sandwiched between an outer polymer film and an inner polymer weave. The pest control material-containing film can also be coated on various materials, such as polymer weaves. The pest control agent-containing film can also be used as a monolayer film. In certain embodiments, the monolayer pest control agent-containing film can be later combined with other films to make laminate products. For example, the monolayer pest-control agent containing film can be combined with an inner film using laminating adhesives. The invention also relates to methods for making the pest control material-containing film and lamination materials of the present invention. The compositions of the present invention preferably are implemented in human and animal food packaging materials in order to safely and efficiently protect the foodstuffs contained therein from insect infestation.

The compositions and methods of the invention have the benefit of extending the life of the active material, i.e., the pest control agent. The lifetimes of the active materials can vary depending on their identity, but when used in the films of present invention, the active materials may remain effective for two years or more.

In one embodiment, the present invention is directed to a pest control composition or methods of producing a pest control composition that includes a lower polymer weave layer, a middle film layer, and an upper polymer film layer. The middle film layer comprises a mixture of a polymer and a pest control agent. The mixture is extruded into a pest control agent-containing film layer. More specifically, in terms of lower range limits, the middle or pest control agent-containing film layer comprises at least 0.01 wt. %, more preferably at least 0.05 wt. %, and most preferably at least 0.1 wt % of the pest control agent based on the total weight of the extruded material. In terms of upper range limits, the middle or pest control agent-containing film layer comprises 10 wt. % or less, more preferably 5 wt % or less, more preferably 1 wt % or less, and most preferably 0.5 wt. % or less of the pest control agent. Thus, a pest control agent-containing film layer according to the present invention may include from 0.01 wt. % to 5 wt. %, from 0.05 wt. % to 1 wt. %, from 0.1 wt. % to 0.5 wt. % of a pest control agent, or any other combination of the above-provided agent range limitations. Ideally, the pest control agent-containing layer comprises from 0.1 wt. % to 1.0 wt. % of a pest control agent.

As used herein, the term "weight percent" means percent, by weight, of a specified composition based on the total weight of the extruded film layer in accordance with the present invention. Similarly, the term "wppm" means parts per million, by weight, of a specified composition based on the total weight of the extruded film layer according to the present invention. Unless otherwise indicated, the terms "weight percent" and "wppm" of a specified composition are based on the total weight of the dry form of the film layer being extruded rather than the total weight post-extrusion.

In another embodiment, the present invention is directed to a pest control composition or methods of producing a pest control composition that includes a lower polymer weave layer which is coated by a film layer comprising a mixture of a polymer and a pest control agent. The mixture is extruded into a pest control agent-containing film layer. More specifically, in terms of lower range limits, the pest control agent-containing film layer comprises at least 0.01 wt. %, more preferably at least 0.05 wt. %, and most preferably at least 0.1 wt % of the pest control agent based on the total weight of the extruded material. In terms of upper range limits, the middle or pest control agent-containing film layer comprises 10 wt. % or less, more preferably 5 wt % or less, more preferably 1 wt % or less, and most preferably 0.5 wt. % or less of the pest control agent. Thus, a pest control agent-containing film layer according to the present invention may include from 0.01 wt. % to 5 wt. %, from 0.05 wt. % to 1 wt. %, from 0.1 wt. % to 0.5 wt. % of a pest control agent, or any other combination of the above-provided pest control agent range limitations. Ideally, the coating layer comprises from 0.1 wt. % to 1.0 wt. % of a pest control agent.

In another embodiment, the invention is directed to a pest control composition or methods of producing a pest control composition comprising pellets comprising a mixture of polymer and pest control agent. The pellets can contain varying amounts of pest control agent. For example, the pellets can contain 25 wt. % or less of the pest control agent, such as 20 wt. % or less, 10 wt. % or less, 5 wt. % or less, 3 wt. % or less, or 1 wt. % or less of the pest control agent. The pellets comprising a mixture of polymer and pest control agent can be created, for example, by combining the desired pest control agent and the desired polymer material, extruding the mixture, and cooling and pelletizing the extruded mixture. In some scenarios, the pellets can be combined with additional polymer and extruded into films and laminate compositions of the present invention. Depending on the amount of pest control agent in the pellets, different amounts of pellets can be combined with additional polymer and extruded. For example, for pellets containing 10 wt. % pest control agent, 1 wt. % (based on the total weight of material fed to the laminating extruder) of these pellets can be combined with additional polymer and extruded into films of the present invention that contain roughly 0.1 wt. % of pest control agent. Or, as another example, pellets containing 5 wt. % pest control agent can be added in an amount of 2 wt. % (based on the total weight of material fed to the laminating extruder) to additional polymer and extruded into films of the present invention that also contain roughly 0.1 wt. % of pest control agent.

A variety of pest control agents may be implemented in the coating layers of the present invention. One example of a pest control agent is a hormone. As used herein, the term "hormone" includes naturally or non-naturally occurring hormones, analogues and mimics thereof. A non-limiting list of types of hormones includes insect growth regulators, juvenile hormones, chitin synthesis inhibitors, ecdysteroids and ecdysone agonists. An exemplary non-limiting list of insect growth regulators includes: buprofezin, cyclopentadecatriene, cydia pmonella granulosis virus, dicyclanil, hexahexyl distannoxane, hexythiazox, Ovex, and poly-i-para-menthene. Particularly preferred hormones suitable for use in the present invention include kinoprene, hydroprene, methoprene, dimilin, fenoxycarb, and pyriproxyfen.

Preferably, the hormone comprises a juvenile hormone. As used herein, the term "juvenile hormone" includes naturally and non-naturally occurring juvenile hormones as well as analogues and mimics thereof. Naturally occurring juvenile hormones are lipophilic sesquiterpenoids containing an epoxide and methyl ester groups. Juvenile hormone analogues are compounds bearing a structural resemblance to the juvenile hormones of insects. A non-limiting list of juvenile hormone analogues suitable for use in the present invention includes: pyriproxyphene: 4-phenoxyphenyl-(RS)-2-2(2-pyridyloxy)propyl ether; fenoxycarb: ethyl {2-(4-fenoxyfenoxy)ethyl}carbamate; kinoprene: 2-propynyl- (E)-3,7,11-trimethyl-2,4-dodecadienoate; methoprene: isopropyl-(2E,4E)-11-methoxy-3,7,11-trimethyl-2,4-dodecadienoate; and hydroprene: ethyl-(E,E)-(R,S)-3,7,11-trimethyldodeca-2,4-dienoate. Thus, a hormone contained in the coating of the present invention may include naturally or non-naturally occurring juvenile hormones such as methoprene, hydroprene, triprene, furnesinic acid ethyl and alkoxy derivatives, pyriproxyfen (Nylar), and fenoxycarb. Particularly preferred juvenile hormones suitable for use in the present invention include kinoprene, hydroprene, methoprene, and fenoxycarb. As methoprene bears a close structural resemblance to naturally occurring juvenile hormones, it is a particularly preferred juvenile hormone of the present invention.

In another embodiment of the present invention, the pest control agent comprises a hormone that comprises a chitin synthesis inhibitor. As used herein, the term "chitin synthesis inhibitor" includes naturally and non-naturally occurring chitin synthesis inhibitors as well as analogues and mimics thereof. Chitin synthesis inhibitors are classified as benzoylphenylureas and possess a number of halogen substituents. The exoskeleton (cuticle) of insects is formed mostly of protein and chitin. Chitin is a polysaccharide of N-acetylglucosamine. During the process of ecdysis, the old cuticle of an insect is shed and a new one is grown. The production of this compound through a polymerization reaction is halted by inhibitor drugs. Without limiting the scope of the present invention to a particular mechanism, the mode of action of these inhibitors is believed to include the blocking of UDP-N-acetylglucosamine transport through the membrane. Without the ability to produce chitin, an insect is unable to hatch or fails to develop due to its malformed cuticle. By retarding the process of chitin growth it is possible to render invertebrates non-viable as reproductive or adult organisms. Chitin synthesis inhibitors may be transferred to insect eggs before deposition from parental blood if the parent insect has ingested the inhibitor or after deposition through contact with a host. Exposed eggs fail to hatch or produce non-viable larvae. A non-limiting list of exemplary chitin synthesis inhibitors includes: triflumeron, chlorfluazuron, lufenuron, teflubenzuron, flufenoxuron, N-2,6-difluorobenzoyl-N'-[2-fluoro-4-(1,1,2,3,3,3-hexafluoropropoxy)phenyl]urea and N-2,6-difluorobenzoyl-N'-[2-fluoro-4-(1,1,2,2-tetrafluoroethoxy-)phenyl]urea, hexaflumuron and other acyl ureas, diflubenzuron (dimilin), and azadirachtin.

Additionally or alternatively, the pest control agent comprises a hormone that comprises an ecdysone agonist. As used herein, the term "ecdysone agonist" includes naturally and non-naturally occurring ecdysone agonists as well as analogues and mimics thereof. Ecdysone agonists are compounds bearing a close resemblance in action to the invertebrate molting hormone ecdysone. The structures of agonists such as RH-2485 (methoxyfenozide), RH-5849 (dibenzoyl hydrazine) and RH-5992 (Tebufenozide), though different from ecdysone, act through the ecdysone receptor at a molecular level and initiate the molting process through gene regulation. Methoxyfenozide, dibenzoyl hydrazine, and Tebufenozide are considered nonsteroidal ecdysone agonists because of their structural variance from ecdysone. However, the pest control agent implemented in the coating of the present invention may be an ecdysteroid hormone, which causes either molting or metamorphosis depending on the stage of the insect, such as ecdysone, 3-dehydroecdysone, Makisterone A, and 20-hydroxyecdysone. Exposure to ecdysone agonists in larvae, prior to their natural ecdysone peak, results in incomplete molting. After ingestion of the compound, the larva begins to develop a new cuticle. However, the new cuticle lacks tanning and the old cuticle fails to be ecdysed/absorbed. Bursicon is the hormone responsible for the tanning and hardening of the cuticle, but to act, it requires the absence of 20-hydroecdysone. Without limiting the scope of the present invention to any particular mechanism, it is believed that the presence of an edysone agonist inhibits bursicon release. As a result, exposed larvae remain in a state of partial molt until death, and are consequently unable to reproduce.

When used as pest control agents, the hormones can be added in any available form. In one embodiment, the hormone is added in liquid form.

Optionally, the films of the present invention include one or more chemical insecticides or microbial pathogens or toxicants as pest control agents. Examples of toxicants include, but are not limited to, borates (boric acid, disodium octaborate tetrahydrate), mirex, sulfuramid and related fluoroalkyl sulfonamides, hydramethylnon, avermectin, A-9248 (diiodomethyl para-tolyl sulfone), fluorosulfonates, imidacloprid, azadirachtin, and cyromazine.

Many of the above-described pest control agents, e.g., methoprene, break down when exposed to UV radiation. As a result, one or more UV protectant materials can optionally be combined with the pest control agent before, during, or after mixing with polymer. The UV protectant materials ideally are non-polymer compositions that absorb UV radiation. Preferably, the pest control agent-containing film layer comprises from about 0.01 wt. % to about 20 wt. %, more preferably from about 0.1 wt. % to about 15 weight percent, and most preferably from about 1 to about 10 wt. % of a UV protectant material. Ideally, the UV protectant material is dispersed throughout the pest control agent/polymer film. However, the UV protectant material may also be contained in a coating layer adjacent to the pest control agent/polymer film. Preferably, this coating layer includes one or more polymers, described herein, which act to support the UV protectant material. In this latter embodiment, the coating layer containing the UV protectant material preferably is oriented externally to the pest control agent-containing film layer in order to reduce exposure of the pest control agent-containing film layer to UV radiation. A non-limiting list of exemplary UV protectant materials that may be included in the films of the present invention includes: benzophenone; hydroxy substituted benzophenones such as 2-hydroxy-4-methoxybenzophenone, 2,2'-dihydroxy-4-methoxybenzophenone, 2-hydroxy-4-acryloyloxyethaxybenzophenone, 2-hydroxy-4-n-octoxybenzophenone and the like; hydroxy phenyl benzopriazdes; substituted acrylonitriles; and selective absorption pigments. A non-limiting list of exemplary selective absorption pigments includes zinc oxide, zinc sulfide, red iron oxide, carbon black, and rutile titanium dioxide. The UV protectant material may also include reflective pigments. Additional UV protectant materials are listed in U.S. Pat. No. 5,965,123, the entirety of which is incorporated herein by reference. Optionally, the pest control agent-containing film also includes one or more pigments so that the coating layers may serve as inks in printing processes.

Additionally, the pest control agent is optionally combined with a rheology additive prior to or while mixing with polymer. Rheology additives increase grease resistance and provide desirable controlled release properties for the pest control agent that is dispersed throughout the polymer. Without limiting the present invention to a particular mechanism, the rheology agent is believed to facilitate retention of the active ingredient in the film, e.g., the pest control agent, by slowly releasing the active to the environment over the product lifetime. That is, the rheology additive facilitates pest control agent migration from within the polymer of the film to the external surface thereof. If a rheology additive is included in the film, the film preferably comprises from about 0.1 wt. % to about 20 wt. %, more preferably from about 0.1 wt. % to about 10 weight percent, and most preferably from about 0.5 wt. % to about 5 wt. % of a rheology additive. Preferably, the rheology additive is a substituted cellulose acetate composition. A non-limiting list of exemplary rheology additives includes cellulose acetate butyrate (CAB) and cellulose acetate proprionate (CAP).

In one embodiment, the polymer and/or pest control agent is mixed with a plasticizer such as an epoxidized soybean oil, e.g., Drapex or phthalate ester. Such plasticizers can be added in a premix with the hormone or can be fed separately from the pest control agent.

As indicated above, the pest control agent-containing film layers of the present invention include a polymer. The polymer can be any polymer that is capable of forming a film upon extrusion. Thus, the polymer in the pest control agent-containing film layer may include one or more of the following polymers: polyethylene, polypropylene, and mixtures thereof, linear low-density polyethylene (LLDPE), low-density polyethylene (LDPE), high-density polyethylene (HDPE), polypropylene (PP), polyethylene-terephthalate (PET), copolymers of polyethylene and polypropylene, and blends thereof. Other polymers, preferably having low densities of, for example, less than 0.93 g/cm$^3$, e.g., less than 0.92 g/cm$^3$, may also be used. During mixing and prior to extrusion, the polymer preferably is in the form of polymer pellets, which are mixed with the pest control agent and subsequently extruded onto a substrate.

In one embodiment, the polymer is a copolymer formed from two or more monomers, optionally selected from the monomers of the polymers identified above. For example, propylene and ethylene.

The polymer in the pest control agent-containing film layer can be polymerized prior to being mixed with pest control agent. Alternatively, final polymerization can take place after the pest control agent has been added to the monomers of the polymer. Additionally, the polymer or monomers of the pest control agent-containing film layer can be in a solid or liquid (melt) form when mixed with pest control agent. In one preferred embodiment, the polymer is polymerized and in a granular solid form before it is mixed with active.

The polymer (or monomers) and pest control agent can be mixed by preblending the materials using agitation and/or heat prior to extrusion. For example, the pest control agent and polymer (or monomers) can be combined and agitated while heating the mixture to, for example, 160° F. (71° C.) or to the softening point of the polymer. This can include the plasticizer, if one is utilized. In another example the pest control agent is mixed with raw polymer pellets in a drum and stirred before being fed to an extruder. In other embodiments, the pest control agent is added directly into the extruder containing the polymer. In such embodiments, the pest control agent can be added, for example, by way of a connection to the throat or just prior to the throat of the extruder. The pest control agent added might be metered using, for example, a metering pump.

In one embodiment of the invention, the polymer and pest control agent can be combined and extruded followed by cooling and pelletizing of the extruded mixture. The pelletized mixture can then later be added to laminating extruders (with or without other polymer) as desired to create pest control structures according to the present invention. As one example, a mixture containing 5-10% by volume or weight of pest control agent and polyethylene and/or polypropylene polymer can be extruded, cooled and pelletized. The pellets containing polymer and pest control agent can be added to a laminating extruder at a level of 1-2% by weight or by volume, for example, along with polymer to create a roughly 0.1% pest control level in the extruded layer.

In one particularly desirable embodiment, the pest control agent-containing film layer of the present invention includes inert dusts such as silica dusts, e.g., diatomaceous earth, and zeolitic compositions (alkali metal aluminum silicates). Diatomaceous earth is made up primarily of amorphous or shapeless silica (silicon dioxide) secreted by diatoms. Preferably, the diatomaceous earth has an average particle size of from about 1 micron to about 50 microns, more preferably from about 5 microns to about 25 microns, and most preferably from about 5 microns to about 15 microns. Particles smaller than 1 micron in diameter are not considered in determining the "average particle size" of diatomaceous earth particles in a diatomaceous earth sample.

Without limiting the operating mechanism of the pest control agent-containing film layers of the present invention, when diatomaceous earth is included in the film, it is believed that the sharp edges inherent to diatomaceous earth may act to irritate or cut the larvae or adult insects that traverse the coating layer. Thus, in one embodiment, the film formulations include an insect-cutting material and/or a larva-cutting material. This irritating or cutting action is believed to facilitate pest control agent delivery to a target organism. As a result, the pest control agent's effects on the target organism can be increased while allowing for decreased pest control agent concentrations in the film layer. The diatomaceous earth that can be implemented in the present invention may originate from mud, seaweed, stagnant water, fresh water or salt water sources. If diatomaceous earth is included in the film layer, the film layer preferably comprises from about 0.01 wt. % to about 20 weight percent, more preferably from about 0.01 wt. % to about 10 weight percent, and most preferably from about 0.1 wt. % to about 5 wt. % of diatomaceous earth. Experimental evidence, provided below, indicates that the combination of a pest control agent with diatomaceous earth in a film layer yields synergistic, surprising and unexpected results over what would be expected by one of ordinary skill in the art based on the effects of these individual components on larvae development and reproductive ability.

As indicated above, the coating compositions of the present invention preferably are implemented in human and animal food packaging materials in order to safely and efficiently protect the foodstuffs contained therein from insect infestation. Thus, the pest control agent-containing film layer can be disposed or adhered on an external surface of a substrate containing human or animal food. An exemplary list of substrates includes cardboard, cloth, bags, wrappers, wood, paper, plastic, and combinations thereof. Specific examples of substrates include food wrappers, cloth bags, stretch film such as is used for holding palletized packaging boxes, bleached paper, clay coated paper, bleached clay coated paper, metalized paper, corrugated boxes, crates, contact paper, shelf paper, and paper linings. In one preferred embodiment, the substrate is a bag such as a wheat or grain storage bag, a burlap bag, a plastic bag, a cloth bag (e.g., formed of cotton or any other textile), or a dog or cat food bag. In a preferred embodiment, the substrate is a polymer weave or a stretch film. Such a polymer weave or stretch film might be made from any of the polymers previously described for mixing in the pest control agent-containing layer.

The pest control agent-containing layers of the present invention may also be incorporated in a laminate material having a plurality of layers. Insects often bore through external layers and, typically, oviposition occurs between layers of a multi-layered material. Accordingly, a film of the present invention preferably is oriented between layers to facilitate delivery of the pest control active ingredient to any eggs or larvae that develop between the layers. In this embodiment, a pest control agent-containing film according to the present invention may be sandwiched between two substrate layers, a first substrate layer and a second substrate layer. Additionally or alternatively, the pest control agent-containing film layer may be formed on the interior surface of the first substrate layer and/or on the external surface of the second substrate layer. In other embodiments, the multi-layer material includes more than two layers in addition to one or more pest control agent-containing layers according to the present invention. The pest control agent-containing film layer can be extruded with the substrate layers or separate from the substrate layers.

In a multilayer structure comprising a pest control agent-containing film layer, other layers can comprise, for example, a polymer weave and/or a polymer film layer. Such layers might be made from any of the polymers previously described for mixing in the pest control agent-containing layer. For example, in one preferred embodiment, the pest control agent-containing film layer is sandwiched between an inner polypropylene weave and an outer polypropylene film.

The present invention is also directed to various methods for preparing film formulations and for applying the coating formulations to substrates to form coating layers. In one embodiment, the method includes the steps of: (a) providing a lower polymer weave; (b) providing an upper polymer film; (c) mixing a pest control agent with a polymer and extruding the mixture between the lower polymer weave and the upper polymer film. Optionally, the extruded material is extruded onto one of the lower polymer weave or the upper polymer film, and the other of the lower polymer weave or the upper polymer film are subsequently sandwiched together with the extruded pest control agent-containing material situated therebetween and adhering the wave and the film to one another. Preferably, the pest control agent included in the mixture is a liquid. Another method involves forming a pest control composition comprising the steps of: (a) providing a lower polymer weave; (b) mixing a pest control agent with a polymer and extruding the resulting mixture with the lower polymer weave. Another method involves mixing a pest control agent with a first polymer composition and extruding the mixture as a monolayer film. Yet another method involves mixing a pest control agent with a first polymer composition and extruding the mixture, cooling the extruded mixture, and pelletizing the cooled, extruded mixture into pellets containing the pest control agent. The pellets containing the pest control agent can be combined with a second polymer composition and extruded as a monolayer or multilayer film.

The present invention will be better understood in view of the following non-limiting examples.

Examples

Performance and Efficacy of Hormone-Containing Film in a Woven Poly Bag Structure Procedure The following example demonstrates the effectiveness of preparing and utilizing a hormone-containing film in a woven polymer bag structure. To prepare the hormone-containing film, liquid methoprene was added to linear low density polyethylene ("LLDPE") pellets in an extruder using a Maguire MPA Peristalic liquid additive pump (MPA-6-18). The methoprene was added to the throat of the extruder via connection tubing and an access plate. A half inch aluminum access plate with a threaded ⅜ connection for the tubing from the metering pump was installed just above the throat of the extruder. The metering pump supply tubing was connected to the plate tube to allow the methoprene to be metered into the extruder as the un-melted LLDPE pellets fall into the extruder. The pump was run on continuous mode at calibration settings for methoprene. The hormone-containing film was sandwiched between an upper film layer and a lower base layer. The upper film structure was a normal reverse printed OPP 0.7 mm film. The base (lower) layer was a polypropylene weave film.

The extrusion process was started with LLDPE until a consistent product was verified.

For Example 1, the pump was set to a methoprene addition rate of 0.5% of the total extrudate volume of 430 lbs/hr (195 kg/hr) at 500 feet per minute (152 m/min) line speed. The process was run for approximately 2 minutes to ensure the mixture was fully incorporated. The example was then carried out over 5 minutes to produce the laminated structure. A 500 lineal foot (152 lineal m) sample of the woven polymer laminate was collected. In addition, the extrusion process was converted to a drool mode so that a 1 lb (0.5 kg) sample of only the hormone-containing extrudate could be retained for active testing. The same procedure was repeated for a second Example 1 run.

Example 2 was carried out in the same manner as Example 1, except that the pump addition level was set to a methoprene addition rate of 1.0% of the total extrudate volume of 430 lbs/hr at 500 feet per minute line speed. The same procedure was repeated for a second Example 2 run.

Example 3 was carried out in the same manner as Examples 1 and 2, except that the pump addition level was set to a blend (50% methoprene/50% Drapex) of 1.0% of the total extrudate volume of 430 lbs/hr at 500 feet per minute line speed. The same procedure was repeated for a second Example 3 run.

The methoprene levels found in the drool run samples was measured. The results are reported in Table 1.

TABLE 1

| Example | Run | Sample Size (g) | Methoprene in extrudate | Methoprene in extrudate (Average of 2 runs) |
|---|---|---|---|---|
| Example 1 | 1 | 3.46 g | 0.107% | 0.103% |
| (0.5% methoprene) | 2 | 4.17 g | 0.100% | |
| Example 2 | 1 | 3.29 g | 0.201% | 0.192% |
| (1.0% methoprene) | 2 | 4.60 g | 0.186% | |
| Example 3 | 1 | 3.54 g | 0.118% | 0.124% |
| (1.0% blend of: 50% methoprene/50% Drapex) | 2 | 3.75 g | 0.129% | |

To achieve target bond pull of 200 g, lower active ingredient (methoprene) levels were used. Examples 4-7 were carried out in the same manner as Example 1-3, except that the pump addition level was set to a methoprene addition rates of 0% for Example 4, 0.1% for Example 5, 0.3% for Example 6, and 0.5% for Example 7 based on the total extrudate volume of 430 lbs/hr at 500 feet per minute line speed. A total of two runs were made with each composition. The bond strength of each run was measured with machine, middle and operator bond pull readings. Bond strengths were measured using a calibrated TMI tensil strength testing device for this purpose. One inch by six inch samples were cut from the operator, middle and machine side of the processed film. These were manually pulled apart and then placed in the tensil testing machine to determine the grams force pull strengths. The results are summarized in Table 2.

TABLE 2

| Example | Run | MACHINE Bond Reading (g) | MIDDLE Bond Reading (g) | OPERATOR Bond Reading (g) |
|---|---|---|---|---|
| Example 4 (0% methoprene) | 1 | 202.3 | 436.2 | 814.5 |
|  | 2 | 269.4 | 352.8 | 276.1 |
| Example 5 (0.1% methoprene) | 1 | 200.8 | 418.0 | 531.3 |
|  | 2 | 275.8 | 356.0 | 298.1 |
| Example 6 (0.3% methoprene) | 1 | 174.4 | 405.3 | 758.8 |
|  | 2 | 222.6 | 336.4 | 659.1 |
| Example 7 (0.5% methoprene) | 1 | 257.3 | 378.1 | 323.7 |
|  | 2 | 263.4 | 299.0 | 280.1 |

As Table 2 shows, in all but one run the bond pull levels met the acceptable value of 200 g. This was despite the MACHINE bond reading to tend toward giving lower bond reading values.

Efficacy Test 1

The efficacy of the hormone-containing films was also evaluated over time. The test was performed by cutting circular sections of the control and hormone-containing packaging films prepared according to the invention as described above to fit the bottom of a plastic Petri dish, about 62 cm$^2$ in area. The dishes were about 2.3 cm (1 inch high). Four-week-old red flour beetle larvae were used as the test insect species. There were four replicates of untreated control, both sides of paper (8 dishes), 10 red flour beetle larvae with ¼ level teaspoon of flour, which is about 1 gram, in each dish. The flour was put in the center of the dish for the larvae to find. In untreated controls, the larvae will often spread the flour over the dish, but with contact insecticides the flour remains clumped in the center. With insect growth regulators such as methoprene, the larvae might find the flour but then adult emergence is inhibited. The flour is necessary to ensure larval survival to the adult stage. A companion set of 4 treatment reps, both sides of paper, was also prepared in the same manner as described above. The dishes were prepared 29 days after the hormone-containing films were produced. The dishes were held at 80 F 60% RH until adult emergence was completed in the controls.

After 19 days, the dishes were observed and adults were noted emerging in the untreated controls. In the treatment dishes, the beetles had remained in the larval stage or were intermediate molts between larvae and pupae or pupae and adult.

28 days after the dishes were prepared, the beetles were counted. The results of the count are reported in Table 3. There were no adults in two of the untreated controls on the outside of the paper. It was speculated that there was some contamination or there is another chemical on the outside that is interfering with the molting process. Of particular interest is the fact that the hormone-containing film seems to be effective on the outside and the inside of the packaging. The counts below show the number of normal healthy adults (from 10 4-week-old larvae) in the Petri dishes, untreated controls outside of paper (UTC-O), untreated controls inside of paper (UTC-I), hormone-containing outside and inside of paper (HC-O and HC-I).

TABLE 3

| Replicate .5% | UTC-O-Control | UTC-I Control | HC-O | HC-I Treated |
|---|---|---|---|---|
| 1 | 7 | 7 | 0 | 0 |
| 2 | 0 | 8 | 0 | 0 |
| 3 | 0 | 9 | 0 | 0 |
| 4 | 5 | 9 | 0 | 0 |

Efficacy Test 2

58 days after the hormone-containing films were prepared a set of Petri dishes was prepared in the same manner as described above for Test 1, except that this time 4-week old confused flour beetle larvae were included along with the red flour beetle.

19 days after preparing the Petri dishes, a count of the beetles was made. The results are shown in Table 4. Again, there were few adults of either species that emerged from the larvae placed either on the outside or inside of the treated packaging. The counts below show the number of normal healthy adults (from 10 4-week-old larvae) in the Petri dishes, untreated controls outside of paper (UTC-O), untreated controls inside of paper (UTC-I), hormone-containing outside and inside of paper (HC-O and HC-I). RFB is red flour beetle, CFB is confused flour beetle. As in the first trial, there appeared to be some contamination on the outside of the packaging, especially in replicate 3 for red flour beetles.

TABLE 4

| Species .5% | Replicate | UTC-O Control | UTC-I Control | HC-O Treated | HC-I Treated |
|---|---|---|---|---|---|
| RFB | 1 | 10 | 9 | 0 | 0 |
|  | 2 | 7 | 9 | 0 | 0 |
|  | 3 | 0 | 4 | 0 | 0 |
|  | 4 | 7 | 8 | 0 | 0 |
| CFB | 1 | 5 | 8 | 0 | 0 |
|  | 2 | 10 | 10 | 0 | 0 |
|  | 3 | 8 | 10 | 0 | 0 |
|  | 4 | 10 | 8 | 0 | 0 |

Efficacy Test 3

A third test was set up using bags treated with 0.1% methoprene 3 months prior. Again the inside (white portion) and outside (printed portion) of the treated bags were used, with ten 4-week old larvae of red flour beetles and confused flour beetles in separate dishes, 5 replicates of each beetle species and bag side. For this trial, circular discs of paper were cut from the bags and taped to the bottom of a Petri dish using double-sided tape. Approximately 2 grams of flour were put in the dish with the 10 larvae. Controls were set up with flour alone on a piece of filter paper. Larvae were held at 27 C (80 F).

An adult beetle count was made 27 days after the dishes were prepared. The counts in Table 5 show the number of normal healthy adults (from 10 4-week-old larvae) in the Petri dishes from untreated controls on filter paper, hormone-containing outside and inside of paper (HC-O and HC-I). RFB is red flour beetle, CFB is confused flour beetle. For this test, some of the CFB larvae exposed on the inside of the bag were able to reach the adult stage. None of the RFB made it to the adult stage. The FIGURE reported below is the number of morphologically-normal adults from the 10 larvae exposed on the papers.

TABLE 5

| Species .1% | Replicate | UTC Control | PG-O Treated | PG-I Treated |
|---|---|---|---|---|
| RFB | 1 | 9 | 0 | 0 |
|  | 2 | 9 | 0 | 0 |
|  | 3 | 10 | 0 | 0 |
|  | 4 | 7 | 0 | 0 |
|  | 5 | 9 | 0 | 0 |
| CFB | 1 | 10 | 1 | 3 |
|  | 2 | 9 | 0 | 5 |
|  | 3 | 10 | 0 | 8 |
|  | 4 | 10 | 0 | 9 |
|  | 5 | 10 | 0 | 7 |

Efficacy Test 4

A fourth efficacy test was conducted to evaluate residual efficacy of packaging material with the insect growth regulator (IGR) methoprene (0.1% active ingredient) incorporated into the laminate exterior of bag packaging. Test insect species are 4-week-old larvae of the red flour beetle (RFB) and the same age larvae of the confused flour beetle (CFB), and late stage nymphs of the psocid species *Lipocelis bostrychophila*, *L. entomophila*, and *L. paeta*. Experiment units for beetles consisted of either the inside or outside of untreated or treated bags placed in the bottom of a 62 cm² Petri dishes (10 mm high), and sealed by caulking around the edges. The same methods were used for dishes containing one of the psocid species, except that the dishes used were 15 mm high and the sides were coated with fluon to try and minimize escape of the psocid nymphs. Ten larvae of either beetle species or ten psocid nymphs of one of the three species were placed in an experimental dish, and there were 6 replicates for the inside and outside of the bags for both the treated bags and the untreated control bags. The criterion for assessment was the emergence of morphologically normal adults of all species.

The outside and the inside of the treated bags showed activity against the RFB larvae and the CFB larvae in the trials (Table 6). No adult RFB emerged from the larvae that were exposed on the treated packaging. There was some emergence of normal adult CFB from larvae exposed on the inside and outside of the bags. This is consistent with previous tests with methoprene that indicate that the CFB is less affected by methoprene compared to the RFB.

TABLE 6

Percentage emergence of morphologically normal adults from the exposure of 10 late-stage larvae of the red flour beetle and confused flour beetle. Untreated controls outside of paper (UTC-O), untreated controls inside of paper (UTC-I), ProvisionGard outside and inside of paper (PG-O and PG-I).

| Month | Species | UTC-O | UTC-I | PG-O | PG-I |
|---|---|---|---|---|---|
| 0 | RFB | 95.0 ± 5.6 | 100 ± 0.0 | 0.0 ± 0.0 | 0.0 ± 0.0 |
|  | CFB | 98.0 ± 4.0 | 100 ± 0.0 | 6.7 ± 6.7 | 41.0 ± 14.7 |

Data for the three psocid species showed mixed results. The psocid nymphs were exposed with cracked wheat, and the nymphs tended to go into the wheat kernels and were difficult to recover. Also, when nymphs were exposed on the inside of the bag, they were able to get under the cross-hatching of the bag, and would go underneath the surface (Table 7). Still, for all three species, there was some reduction in adult emergence on the outside treated bags compared to the control bags, and even a reduction on the inside of the treated bags for two species.

TABLE 7

Percentage emergence of morphologically normal adults from the exposure of 10 late-stage nymphs of three psocid species. Untreated controls outside of paper (UTC-O), untreated controls inside of paper (UTC-I), ProvisionGard outside and inside of paper (PG-O and PG-I).

| Month | Species | UTC-O | UTC-I | PG-O | PG-I |
|---|---|---|---|---|---|
| 0 | L. bostrychophila | 95.0 ± 4.2 | 80.0 ± 6.3 | 43.3 ± 18.0 | 43.3 ± 18.0 |
|  | L. entomophila | 75.0 ± 8.8 | 75.0 ± 6.2 | 33.3 ± 7.6 | 40.0 ± 8.2 |
|  | L. paeta | 53.0 ± 6.7 | 50.0 ± 5.7 | 26.7 ± 13.0 | 41.7 ± 7.4 |

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

I claim:

1. A method for forming a pest control composition, the method comprising the steps of:
   mixing a juvenile hormone pest control agent with a first polymer composition and extruding the mixture,
   cooling the extruded mixture,
   pelletizing the cooled, extruded mixture into pellets containing the juvenile hormone pest control agent,
   extruding the pellets containing the juvenile hormone pest control agent to form an extrusion product comprising a film, and
   forming a package structure comprising an outer polymer layer having a first surface that is exposed and a second surface, an intermediate layer adjacent to the second surface comprising the extrusion product, and a base layer adjacent to the intermediate layer and opposite the second surface; wherein the base layer comprises a woven polymer, and wherein the outer polymer layer is bonded to the intermediate layer using laminating adhesive.

2. The method of claim 1, further comprising combining as a blend the pellets containing pest control agent with a second polymer composition and extruding the blend as a film to form the extrusion product.

3. The method of claim 2, wherein the blend is extruded as a monolayer film.

4. The method of claim 3, further comprising combining the monolayer film with another film using a laminating adhesive.

5. The method of claim 1, wherein the pest control agent is mixed with raw polymer pellets of the first polymer composition and stirred before being fed to an extruder.

6. The method of claim 1, wherein the pest control agent is added directly into an extruder containing the first polymer composition.

7. The method of claim 1, wherein the pest control agent is added at a concentration of between 0.01 wt. % and 5 wt. % based on the total weight of the extruded mixture.

8. The method of claim 1, wherein the pest control agent is added in a liquid form.

9. The method of claim 1, wherein the pest control agent is hydroprene, methoprene, kinopren, triprene, or pyriproxyfen.

10. The method of claim 1, wherein the pest control agent is methoprene.

11. The method of claim 1, wherein a UV protectant material is added to the pest control agent and first polymer composition mixture.

12. The method of claim 1, wherein a rheology additive is added to the pest control agent and first polymer composition mixture.

13. The method of claim 1, wherein an inert dust is added to the pest control agent and first polymer composition mixture.

14. The method of claim 1, wherein the pest control agent comprises an insecticide.

15. A pest control composition prepared according to the method of claim 1.

16. The method of claim 13, wherein the inert dust is a silica dust.

* * * * *